United States Patent [19]

Nakajima et al.

[11] 3,959,245

[45] May 25, 1976

[54] L-ASPARTYL-AMINOMALONIC ACID METHYL 2-METHYLCYCLOHEXYL DIESTER

[75] Inventors: Nobuo Nakajima, Nishinomiya; Hisashi Aoki, Suita; Masahiko Fujino, Takarazuka; Osamu Nishimura, Toyonaka; Mitsuhiro Wakimasu, Suita; Mitsuhiko Mano, Settsu, all of Japan

[73] Assignee: Takeda Chemical Industries, Ltd., Osaka, Japan

[22] Filed: Mar. 27, 1973

[21] Appl. No.: 345,328

[30] Foreign Application Priority Data
Mar. 29, 1972  Japan............................ 47-31485
Mar. 30, 1972  Japan............................ 47-32007

[52] U.S. Cl............................ 260/112.5 R; 426/548
[51] Int. Cl.²................ A23L 1/22; C07C 103/52
[58] Field of Search............................ 260/112.5

[56] References Cited
UNITED STATES PATENTS 3,492,131  1/1970  Schlatter........................ 260/112.5
3,798,206  3/1974  Uchiyama et al................ 260/112.5
3,799,918  3/1974  Mazur.............................. 260/112.5
3,801,563  4/1974  Nakajima et al................. 260/112.5
3,808,190  4/1974  Dahlmans et al................ 260/112.5
3,833,553  9/1974  Ariyoshi et al.................. 260/112.5

OTHER PUBLICATIONS

Schroeder and Lubke, "The Peptides," Vol. 1, Academic Press, New York, (1965), pp. 122–124.

Bailey, J. Chem. Soc., 1950, 3461–3466.

*Primary Examiner*—Lewis Gotts
*Assistant Examiner*—Reginald J. Suyat
*Attorney, Agent, or Firm*—Wenderoth, Lind & Ponack

[57] ABSTRACT

A novel dipeptide, L-aspartyl-aminomalonic acid methyl 2-methylcyclohexyl diester and its physiologically acceptable salts which are useful as a sweetener, and production thereof and sweetening compositions containing the dipeptide or its salt.

1 Claim, No Drawings

L-ASPARTYL-AMINOMALONIC ACID METHYL 2-METHYLCYCLOHEXYL DIESTER

This invention relates to a novel dipeptide, L-aspartylaminomalonic acid methyl 2-methylcyclohexyl diester and its physiologically acceptable salts which are useful as a sweetener, the dipeptide having the formula;

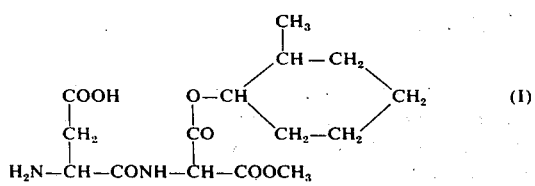

In the course of extensive studies on sweeteners, the present inventors suceeded in the synthesis of the novel compound (I) and found (1) that the compound (I) shows sweetness as high as at least 6600 times as that of sucrose, (2) that the sweetness of the compound (I) is of high quality which is free from bitterness produced by the known sweeteners (e.g. saccharin sodium), (3) that the 2-methylcyclohexyl group is essential for the sweetness of the compound (I) and (4) that the compound (I) is safely used as a sweetener.

On the basis of the unexpected findings, the present inventors have made further studies on the compound (I) and completed the invention.

The principal object of the present invention is to provide the compound (I) and its physiologically acceptable salts.

The second object of the present invention is to provide a process for production of the compound (I) and its salts.

Another object of this invention is to provide sweetening compositions containing the compound (I) or its salt as a main ingredient.

Further object of the present invention is to provide foods sweetened by the compound (I) or its salt, The present compound (I) is produced by a process conventional per se in the field of peptide synthesis and typical examples are mentioned below:

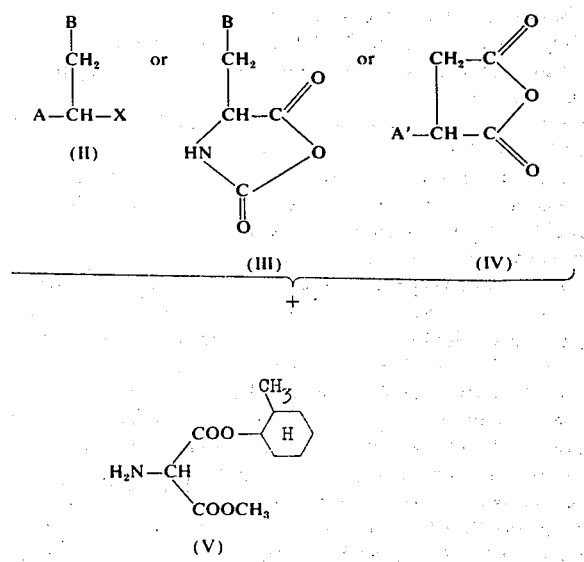

- A,A': protected amino group
- B : protected carboxyl group
- X : carboxyl group which may be activated The compound (I) is prepared, for example, by reacting the compound (II), (III) or (IV) with the compound (V) and removing the protective group(s) from the resulting compound.

The protective group of the protected amino group A of A' in the formula (II) or (IV) is a group that may be ultimately removed by deblocking reactions. A number of such removable protective groups have been developed in the field of peptide synthesis and they may be suitably utilized in the present process. Examples of the protective groups of the protected amino group are benzyloxycarbonyl, t-butyloxycarbonyl, p-chlorobenzyloxycarbonyl, t-amyloxycarbonyl, formyl and so forth. It should be additionally noted that as the group A', there may be mentioned a group represented by Y·NH$_2$— wherein Y is a strong acid such as an inorganic acid (e.g., hydrogen chloride or hydrogen bromide) or an organic acid (e.g. benzenesulfonic acid or p-toluenesulfonic acid).

The protective group of the protected carboxyl group B in the formula (II) or (III) may be selected from among the numerous groups which have heretofore been established. Examples of such groups are benzyl, p-nitrobenzyl, p-chlorobenzyl, t-butyl and so forth.

As to the activated carboxyl group represented by X, there also have been reported a number of species and, here again, these established species may be suitably employed in the present process. Such activated carboxyl groups may be exemplified by the corresponding chloride, azide, mixed anhydride with e.g. a carbonic acid mono-alkyl ester and activated ester (e.g. p-nitrophenyl ester, 2,4,5-trichlorophenyl ester, pentachlorophenyl ester, N-hydroxysuccinimide ester, N-hydroxy-5-norbornene-2,3-dicarboximide or N-hydroxybenztriazole ester).

The present reaction is generally conducted at a low temperature of about —5°C to about 10°C. However, under certain circumstances, the reaction may be conducted either heating or at a still lower temperature of about —20°C.

The reaction is generally conducted in the presence of a suitable solvent such as tetrahydrofuran, dioxane, dimethylformamide, methylene chloride, chloroform and a mixture of these solvent with water.

The compound (V) is employed in an amount approximately equimolar relative to the compound (II), (III) or (IV), though this ratio need not be strictly adhered to.

The present process may be conducted in the presence of a dehydrating agent such as carbodiimide reagent (e.g., dicyclohexylcarbodiimide or water-soluble carbodiimides). The dehydrating agent is employed generally in an amount of equivalent or twice mole with respect to the theoretical amount of water that will be by-produced.

After the reaction has been completed, if the reaction product has protective group(s), such group(s) may be removed to yield the desired compound. In the field of peptide synthesis, there are available a number of expedient procedures for removal of protective groups, each procedure being tailored to one protective group or another and these established procedures may be utilized with advantage in the working of this invention.

For example, catalytic hydrogenolysis with palladium black or palladium-on-carbon may be mentioned. Generally these reactions proceed to satisfactory extent at room temperature, though they may be conducted under cooling. These reactions are generally conducted in the presence of a suitable solvent. The solvent is exemplified by water, methanol, ethanol, dioxane, tetrahydrofuran, acetic acid, t-butanol, isopropanol and so forth.

After the above reactions, the product can be purified and isolated by procedures which are conventional per se, e.g. phasic transfer, concentration, chromatography, crystallization, recrystallization and the like.

While the objective compound is in many instances obtained in the free form, it may be isolated as the corresponding acid addition salt of a mineral acid such as hydrochloric acid, sulfuric acid, hydroiodic acid or hydrobromic acid or of an organic acid such as p-toluenesulfonic acid, trichloroacetic acid, trifluoroacetic acid or formic acid; the corresponding salt of an alkali metal such as sodium, potassium or lithium or of an alkaline earth metal such as calcium or magnesium; or the corresponding ammonium salt.

Referring to the 2-methylcyclohexyl group of the objective compound of this invention, the carbon atom in 2-position to which the 2-methyl group is attached is an asymmetric carbon atom and said methyl group and the oxycarbonyl group in 1-position are in cis-trans relation. Therefore, the compound of this invention includes four isomers, d-cis, l-cis, d-trans and l-trans. The starting material aminomalonic acid methyl 2-methylcyclohexyl diester similarly comprises four isomers and since it is generally used as a mixture of these isomers, the product is also a mixture of four isomers. However, by resolution, one may obtain any of these isomers individually or a mixture of two or three of them.

L-Aspartyl-aminomalonic acid methyl 2-methylcyclohexyl diester which is obtainable as above is not only useful as a sweetener of low toxicity but also of use as an intermediate for the synthesis of various peptides.

EXPERIMENT 1

L-Aspartyl-aminomalonic acid methyl 2-methylcyclohexyl diester was dissolved in water and the threshold values were determined by the method of limit.

| | |
|---|---|
| Difference threshold (the lowest concentration at which the sample can be distinguished from distilled water) | 0.00005% |
| Taste threshold (the lowest concentration at which the sample tastes sweet) | 0.00013% |

EXPERIMENT 2

Using 0.0010% and 0.0020% aqueous solutions of L-aspartyl-aminomalonic acid methyl 2-methylcyclohexyl diester as reference samples and aqueous solutions of sucrose of 5 different concentrations as matching samples, an organoleptic test was performed using a panel of 50 trained tasters.

Probit analysis of the scores yielded the following sucrose-equivalent concentrations.

| Reference sample(%) | Equivalent concentration of sucrose with respect to reference sample(%) | Sweetness with respect to sucrose(times) |
|---|---|---|
| 0.0010 | 6.6 | 6600 |
| 0.0020 | 10.8 | 5400 |

The dipeptide compounds are found to be nontoxic by the toxicity tests by the oral administration of the dipeptide compounds to mice, and the dipeptide compounds of the present invention can be used as such or added to foods in the same manner as the conventional sweetener saccharin sodium.

The most effective amount of the dipeptide compound to be employed varies with kinds of foods to be sweetened, and usually about 0.00005 to about 0.2% by weight relative to foods as served to mouth. An amount over 0.2% is superfluous for the increase of sweetness and an amount below about 0.00005% is by itself not sufficient to sweeten foods.

It should be noted that an amount of the physiologically acceptable salt of the dipeptide is calculated in terms of the peptide.

The foods to which this invention is applicable include various powdery, liquid and solid foods in which sweeteners are usually incorporated. For example, varieties of foods of farm, aquatic, forestal and animal origins such as alcoholic beverages, e.g. refined sake, compound sake, fruit sake (including sweetened fruit sake), beer, Western-style alcoholic beverages, sweet sake, etc.; nonalcoholic beverages, e.g. fruit juices, imitation juices, 'lactobacillus' drinks; instant foods including instant juices, instant coffee, powdered red bean drink, etc.; foods marketed in polyethylene or other synthetic resin pouches, such as fruits in syrups, syrups, foods soaked in fruit syrups; soy, sauces, vinegar, dressings, mayonnaise, ketchups, curry rice, soups, premixed seasonings, powdered soy, powdered soybean paste; rice balls, rice cakes, bread confections, Japanese-style cakes, biscuits, crackers, hot cake mix, chocolate, caramel, candies, chewing gum, jellies, puddings, bean jam, candied fruits and vegetables, fresh cream, fruit jams, marmalades, flour paste; diary products such as formulated powdered milk, ice cream, etc.; sherbet; man-made meat; bottled vegetables, fruits and other produces; canned foods; soy-cooked farm produces including soy-cooled beans and meat, agricultural gourmet foods, cooked vegetable farm products, pickled farm products, smoked fish and meat, such meat products as bacons, hams, sausages, etc.; whale meat products; processed fish pastes such as fish ham, fish sausage, etc.; salted sea-urchins and other marine products, pickled fish roes and other processed fish roes, dried fish, frozen foods, pickled or otherwise cured seaweeds, cured meat, salted soy-cooked seatangle, soy-cooked laver and other seaweeds, other cooked foods, aquatic gourmet foods, seaweed gourmet foods, seasoned laver, canned aquatic and animal products; compound condiments, compound sweeteners; such luxury items as tobacco, arious drugs including dentifrices; and so forth. In addition to these foods, this invention is applicable to all other foods only if the object of this invention can be accomplished.

As regards the mode of incorporation of the present dipeptide compounds into foods, any of the procedures routinely employed in the production of foods, such as blending, admixing, dissolution, soaking, impregnation, dusting, spraying, injection, etc., can be utilized.

As regards the timing of addition to foods, the present compounds may be added in the course of production of such foods and, preferably, is at a time towards the end of processing. In other words, they may be added in the same manner as saccharin sodium. For example, in the case of cooked foods such as a curry roux, the compounds are preferably added uniformly at the end of heating or after heating.

The dipeptide compounds themselves have strong ability of sweetening foods and it is often difficult to weigh the necessary amount of the dipeptide ester compound to efficiently sweeten foods. Therefore, there is demanded to provide the sweetening compositions in which the dipeptide ester compound is appropriately diluted. Such a composition convenient for handy and practical use is prepared by incorporating at least one dipeptide ester compound with suitable solid carrier or liquid carrier which is known per se as adjuvants.

Such a solid carrier is exemplified by carboxymethylcellulose, glucose, lactose, dextrin, their mixture or the like. The liquid carrier is exemplified by water, ethanol propylene glycol, their mixture or the like.

It is also possible to use the present dipeptide compounds in combination with other known additives for foods, e.g. sweeteners (such as sucrose, fructose, glucose, ribose, xylose, sorbitol, maltitol, saccharin, glycine, alanine, glycyrrhizin, and the like), essences, food colors, and the like. Those additives are to be construed as "carrier" or "adjuvant" in the present invention.

For preparing the composition matter, any of conventional means are employed, and for example, the dipeptide compounds are formulated by mixing the dipeptide compound with the carrier or carriers into solid compositions (e.g. powders, granules and the like), liquid compositions (e.g. solutions, syrups and the like), etc.

The amount of the dipeptide and its physiologically acceptable salt to be incorporated in the sweetening composition is usually about 0.01% to about 10% by weight of the composition, the amount of the salt being calculated in terms of the dipeptide.

This invention will be further illustrated by way of Examples. In those examples, the term "part(s) by weight" has the same relationship to the term "part(s) by volume" as do "gram(s)" to "milliliter(s)."

EXAMPLE 1

1. Preparation of carbobenzoxyaminomalonic acid methyl 2-methylcyclohexyl diester In 20 ml of dry ethyl ether is dissolved 2.68 g. of carbobenzoxyaminomalonic acid monomethyl ester and under cooling with ice and stirring, 2.29 g. of phosphorus pentachloride is added. Then, at room temperature, the mixture is stirred for 30 minutes. Meanwhile, 7.0 g. of pyridine is added to 2.29 g. of 2-methylcyclohexanol and, under cooling with ice and stirring, the above-prepared acid chloride solution is added dropwise over 30 minutes. Then, at room temperature, the mixture is stirred for 1 hour and the by-product pyridine hydrochloride is filtered off. The ethereal solution is washed with a 10% aqueous solution of citric acid (30ml ×3), a saturated aqueous solution of sodium hydrogen carbonate (30ml ×3) and a saturated aqueous solution of sodium chloride (30ml ×3). After drying over anhydrous sodium sulfate, the solvent is distilled off under reduced pressure and the residue is crystallized from ptroleum ether. Scales are obtained upon recrystallization from ethyl ether-petroleum ether.

Yield 2.35 g. (64.7%); m.p.62°–64°C; analysis: calcd. for $C_{19}H_{25}O_6N$ : C, 62.79; H, 6.93; N, 3.85; found C, 62.66; H, 6.93; N, 3.86.

2. Preparation of carbobenzoxy-β-benzyl-L-aspartylaminomalonic acid methyl 2-methylcyclohexyl diester In 50ml of methanol is dissolved 2.00 g. of carbobenzoxy-aminomalonic acid methyl 2-methylcyclohexyl diester and the solution is subjected to catalytic reduction with palladium black at atmospheric pressure for 4 hours. The catalyst is removed by filtration and the solvent is evaporated under reduced pressure and the residue is dissolved in 20ml of dioxane. Meanwhile, 1.7 g. of carbobenzoxy-L-aspartic acid β-benzyl ester is dissolved in 20ml of dioxane, followed by the addition of 0.99 g. of N-hydroxy-5-norbornene-2,3-dicarboximide. While the mixture is cooled with ice and stirred, 1.14 g. of dicyclohexylcarbodiimide is added. Then, at room temperature, the mixture is stirred for 4 hours. The by-product dicyclohexylurea is filtered off and, under cooling with ice and stirring, the filtrate is added to the above-prepared amine solution. Then, at room temperature, the mixture is stirred overnight. The solvent is distilled off under reduced pressure and the residue is dissolved in 50ml of ethyl ether. The solution is washed with a saturated aqueous solution of sodium hydrogen carbonate (30ml ×3), 1N hydrochloric acid (30ml ×3) and a saturated aqueous solution of sodium chloride (30ml ×3). After drying over anhydrous sodium sulfate, the solvent is distilled off under reduced pressure and the residue is purified by column chromatography on silica gel to yield a colorless oil. Yield 2.20g. (77.4%).

3. Preparation of L-aspartyl-aminomalonic acid methyl 2-methylcyclohexyl diester In 50ml of methanol is dissolved 1.80 g. of carbobenzoxy-β-benzyl-L-aspartyl-aminomalonic acid methyl 2-methylcyclohexyl diester and the resulting solution is subjected to catalytic reduction with palladium black at atmospheric pressure for 2.5 hours. The catalyst is filtered off and the solvent is distilled off under reduced pressure. The residue is dissolved in 20ml of benzene and the solution is filtered. The solvent is distilled off under reduced pressure and dry ethyl ether is added to the residue. The procedure yields a white gel.

Yield 0.98 g. (85.8%); m.p.88°–94°C; analysis: calcd. for $C_{15}H_{24}O_7N_2$: C, 52.32; H, 7.03; N, 8.14; found C, 52,42; H, 7.32; N, 7.83.

EXAMPLE 2

Preparation of L-aspartyl-aminomalonic acid methyl 2-methylcyclohexyl diester

In 60ml of methanol is dissolved 3.63 g. of N-carbobenzoxy-aminomalonic acid methyl 2-methylcyclohexyl diester and the solution is subjected to catalytic reduction with a suitable amount of palladium black in hydrogen streams. The palladium black is filtered off and the methanol is distilled off under reduced pressure to yield a colorless oil.

This oil is dissolved in 50ml of methylene chloride and, at −50°C, 1.40ml of triethylamine is added. Meanwhile, 1.59 g. of L-2,5-oxazolidinedione-4-acetic acid, which has been prepared by the routine procedure, is dissolved in 30ml of methylene chloride and after cooling to −50°C, the solution is added dropwise to the above-prepared solution. The reaction is conducted at −50°C for 3 hours and, then, at room temperature overnight. Next morning, the methylene chloride is distilled off under reduced pressure and the residue is dissolved in a small amount of water. The solution is purified by column chromatography on Sephadex G-10(registered trade name of the resin produced by Pharmacia Fine Chemicals, Sweden). Then, the water is distilled off under reduced pressure and dry ethyl ether is added, whereupon precipitates separate out. Yield 0.78 g. (32%).

EXAMPLE 3

Preparation of L-aspartyl-aminomalonic acid methyl 2-methylcyclohexyl diester

By the same procedure as Example 2, 3.63 g. of N-carbobenzoxy-aminomalonic acid methyl 2-methylcyclohexyl diester is catalytically reduced to obtain a colorless oil. This oil is dissolved in 20ml of ethyl acetate, followed by the addition of 1ml of a 2.5M aqueous solution of potassium carbonate. Meanwhile, 2.49 g. of N-carbobenzoxy-L-aspartic anhydride prepared by the routine procedure is added to the above solution of 20°C and the mixture is stirred for 2 hours. To the reaction mixture is added 30ml of water and the water layer is washed with ethyl ether (20ml ×3) and acidified with 1N hydrochloric acid. The oily precipitate is extracted with ethyl ether (30ml ×3). After the ethereal solution is dried over anhydrous sodium sulfate, the solvent is distilled off under reduced pressure, whereupon a colorless oil is obtained. By thin-layer chromatography, this product is shown to be a mixture of α-and β-peptides. Without separating them, the oily product is dissolved in 60ml of methanol and catalytically reduced in hydrogen streams in the presence of palladium black at atmospheric pressure. The palladium black is filtered off and the methanol is distilled off under reduced pressure.

To the residual oil is added 50ml of dry ethyl ether, whereupon a precipitate separates. Yield 2.62 g. (76%).

By thin-layer chromatography, this product is shown to be a mixture comprising, predominantly, α-peptide and, in a minor proportion, β-peptide,

EXAMPLE 4

Preparation of L-aspartyl-aminomalonic acid methyl 2-methylcyclohexyl diester

In a mixture of 50ml of ethyl acetate and 10ml of acetic acid is dissolved 2.3 g. of aminomalonic acid methyl 2-methylcyclohexyl diester, and 1.5 g. of aspartic anhydride hydrochloride is added. The mixture is stirred at room temperature for 2 hours and concentrated under reduced pressure. The residue is crystallized from petroleum ether-ethyl ether to give crystals of a mixture of α- and β-peptide. Yield 3.6 g. (95%). The crystals are dissolved in cold water and neutralized with sodium hydroxide, whereupon the α-peptide is separated as crystals of the monohydrate. Yield 1.8 g. (50%) m.p123°–124°C (from water)

EXAMPLE 5

By the routine procedure, 1 kg. of powder consisting of, by weight, 6% of mandarin orange juice (1/5 conc.; race: Unshu), 5% of citric acid, 1.2% of powdery orange spice, 0.6% of vitamin C, 0.1% of food color of yellow and the rest of lactose is evenly blended with 0.1 g. of L-aspartyl-aminomalonic acid methyl 2-methylcyclohexyl diester to prepare a powdered orange juice. This powdery juice has a good quality of sweetness and is stable quality-wise.

EXAMPLE 6

Five kg. of apples are processed in the routine manner to obtain an apple pulp. The, 1.5 kg. of the apple pulp, 0.6 kg. of 75% sorbitol solution, 0.01 kg. of caboxymethyl-cellulose sodium and 0.2 g. of L-aspartylaminomalonic acid methyl 2-methylcyclohexyl diester are compounded in the routine manner to prepare an apple jam. This product is good in both sweetness and flavor.

EXAMPLE 7

By weight, 23 parts of cacao paste, 17 parts of cacao butter, 25 parts of sucrose, 8 parts of sorbitol powder, 18 parts of dried full cream milk, 2 parts of lecithin as an emulsifier, spice and others and 0.004 part of L-aspartylaminomalonic acid methyl 2-methylcyclohexyl diester are compounded in the routine manner to prepare a chocolate. This product features a good balance of sweetness and flavor and is highly delicious.

EXAMPLE 8

In the routine manner, an ice-cream mix is prepared by compounding 200 g. of fresh cream, 95 g. of dried separated milk, 50 g. of powdery sorbitol, 50 g. of millet jelly, 2 g. of sorbitan fatty acid ester, 3 g. of sodium alginate, 0.04 g. of L-aspartyl-aminomalonic acid methyl 2-methylcyclohexyl diester and 500 ml of water and a small portion of essence. This product is excellent in both sweetness and flavor.

EXAMPLE 9

By weight, 50 parts of dicalcium phosphate, 28 parts of glycerin, 1.5 part of fatty acid monoglyceride, 1.5 part of sodium laurylsulate, 1 part of carboxymethyl-cellulose, 0.003 part of L-aspartyl-aminomalonic acid methyl 2-methylcyclohexyl diester, a small amount of spice and 17.5 parts of water are compounded and kneaded to prepare a tooth paste in the routine manner. This dentifrice has a refreshing quality of sweetness and tastes good and spicy.

EXAMPLE 10

By the routine procedure, 300,000 I.U. of vitamin A (palmitate), 30,000 I.U. of vitamin D, 1.5 g. of polyoxyethylene(20) sorbitan monooleate, 0.1 g. of orange oil, 25 g. of sucrose, 1.5 g. of sorbitol, 0.015 g. of L-aspartyl-aminomalonic acid methyl 2-methylcyclohexyl diester and the balance of distilled water to make 100ml are compounded together to obtain a vitamin A/D syrup. This product has a refreshing quality of sweetness and is easy to take by the mouth.

EXAMPLE 11

By weight, 50 parts of ribose, 49.8 parts of lactose and 0.2 part of L-aspartyl-aminomalonic acid methyl 2-methylcyclohexyl diester are evenly compounded in the routine manner to prepare a sweetening composition. This product is about 10 times as sweet as sucrose and has an excellent quality of sweetness.

What we claim is:

1. L-aspartyl-aminomalonic acid methyl 2-methylcyclohexyl diester and its physiologically acceptable salts.

* * * * *

UNITED STATES PATENT OFFICE
CERTIFICATE OF CORRECTION

Patent No. 3,959,245  Dated May 25, 1976

Inventor(s) Nobuo Nakajima, et al

It is certified that error appears in the above-identified patent and that said Letters Patent are hereby corrected as shown below:

The term of this patent subsequent to April 2, 1991, has been disclaimed.

Signed and Sealed this

Sixth Day of July 1976

[SEAL]

Attest:

RUTH C. MASON
Attesting Officer

C. MARSHALL DANN
Commissioner of Patents and Trademarks